United States Patent [19]

Levin

[11] Patent Number: 4,945,245
[45] Date of Patent: Jul. 31, 1990

[54] EVANESCENT WAVE BACKGROUND FLUORESCENCE/ABSORBANCE DETECTION

[76] Inventor: Herman W. Levin, 1919 Chestnut St. #2706, Philadelphia, Pa. 19103

[21] Appl. No.: 305,027

[22] PCT Filed: Jan. 14, 1987

[63] Continuation-in-part of Ser. No. 818/721, Jan. 14, 1986, abandoned.

[86] PCT. No.: PCTUS87/00088

§ 371 Date: Jul. 14, 1988

§ 102(e) Date: Jul. 14, 1988

[87] PCT Pub. No.: WO87/04247

PCT Pub. Date: Jul. 16, 1987

[51] Int. Cl.$^5$ .................... G01N 21/64; G01N 33/551
[52] U.S. Cl. ................ 250/461.2; 250/458.1; 250/459.1; 250/461.1; 436/527
[58] Field of Search ............ 250/461.2, 461.1, 459.1, 250/458.1; 436/527, 805, 807; 422/57

[56] References Cited

U.S. PATENT DOCUMENTS

| | | | |
|---|---|---|---|
| 3,604,927 | 9/1971 | Hirschfeld | 250/483.1 |
| 3,992,631 | 11/1976 | Harte | 250/365 |
| 4,040,691 | 8/1977 | David et al. | 356/201 |
| 4,050,895 | 1/1977 | Haray et al. | 23/230 |
| 4,100,416 | 7/1978 | Hirschfeld | 250/461.2 |
| 4,321,057 | 3/1982 | Buckles | 435/4 |
| 4,399,099 | 8/1983 | Buckles | 422/58 |
| 4,400,056 | 8/1983 | Gelo | 350/96.19 |
| 4,447,546 | 5/1984 | Hirschfeld | 436/527 |
| 4,451,149 | 5/1984 | Noeller | 356/317 |
| 4,558,014 | 12/1985 | Hirschfeld et al. | 436/127 |
| 4,582,809 | 4/1986 | Block et al. | 436/527 |
| 4,608,344 | 8/1986 | Carter et al. | 436/34 |
| 4,768,513 | 9/1988 | Suzuki | 128/634 |
| 4,818,710 | 4/1989 | Sutherland et al. | 436/527 |

FOREIGN PATENT DOCUMENTS

87/04247  7/1987  World Int. Prop. O. ....... 250/461.1

OTHER PUBLICATIONS

R. T. Gallagher, Sensors Exploit Optical Fiber's Physical Sensitivity, Electronics (21 Apr. 1983), pp. 85–92.
L. M. Johnson et al., An Integrated Optical Temperature Sensor, MIT Industrial Liason Propgram Report 5-38-81.
J. S. Schultz & G. Sims, Affinity Sensors for Individual Metabolites. Chem. Abstr., 92: 193820y (1980).
P. L. Smock, et al., Vapor Phase Determination of Blood Ammonia by an Optical Waveguide Technique Analytical Chem. v. 51, No. 4 (Apr. 1979), pp. 505–508.
E. E. Hardy, et al., Coated Optical Guides for Spectro- (List continued on next page.)

Primary Examiner—Constantine Hannaher
Attorney, Agent, or Firm—Elman & Wilf

[57] ABSTRACT

It is proposed to increase the utility of intracellular fluorescence and absorbance measurements for control of fermentation and cell culture by correcting on-line for background fluorescence of the media, also to be able to measure the fluorescence or absorbance of the fluid media in the presence of suspended cells or particles. The measurements could be extended to measure the optical properties of other fluids which contain suspended particles. This invention uses the characteristics of the evanescent wave at the surface of an optic waveguide. The wave penetrates into the less dense medium only to about the depth of about ½ wavelength. The thickness of media swept by the evanescent wave is much less than the size of a cell, thereby essentially separating the fluorescence or absorbance of the media from that of the cells. Apparatus is disclosed for carrying out the methods taught herein, including the use of an optical fiber to generate the evanescent wave and the use of a flat plate waveguide to generate it. Apparatus that can read both bulk fluorescence and evanescent wave fluorescence employs a flat plate waveguide to generate the evanescent wave and fiber optics to create an alternating dual-beam approach to generating both sets of data.

13 Claims, 7 Drawing Sheets

OTHER PUBLICATIONS photometry of Chemical Reactions, Nature v. 257 (23 Oct. 1975), pp. 666–667.

V. Ya. Popov, et al., Investigation of Monomolecular Layers of Immunoglobulin G by an Infrared Spectroscopy Method, Biofizika, v. 27, No. 4 (1982), pp. 604–607.

N. L. Thompson, Surface Binding Rates of Nonfluorescent Molecules May Be Obtained by Total Internal Reflection with Fluorescence Correlation Spectroscopy, Biophys. J., v. 38 (Jun. 1982), pp. 327–329.

R. M. Weis et al., J. Biol. Chem., v 257, No. 11 (10 Jun. 1982), pp. 6440–6445.

B. Chance and B. Thorell, Fluoresecence Measurement of Mitochondrial Pyridine Nucleotide in Aerobiosis and Anaerobiosis, Nature, v. 184, No. 4691 (26 Sep. 1959), pp. 931–934.

L. N. M. Duysens & J. Amesz, Fluorescence Spectrophotometry of Reduced Phosphopyridine Nucleotide in Intact Cells in the Near-Ultraviolet and Visible Region, Biochim. et Biophys. Acta, v. 24 (1957), pp. 19–26.

B. Thomasset et al., Fluorescence and Photoacoustic Spectroscopy of Immobilized Thylakoids, Biotechnology & Bioengineering, v. 25 (1983), pp. 2453–2458.

K. Gschwend, et al., Detection of Reactor Nonhomogeneities by Measuring Culture Fluorescence, Biotechnology & Bioengineering, v. 25 (1983) pp. 2789–2793.

A. Mayevsky & B. Chance, Intracellular Oxidation-Reduction State Measure in situ by a Multichannel Fiber-Optic Surface Fluorometer, Science, v. 217 (6 Aug. 1982), pp. 537–540.

W. Beyeler et al., On-Line Measurements of Culture Fluorescence: Method & Application, Eur. J. Appl. Microbiol. Biotechno., v. 13 (1981) pp. 10–14.

C. M. Watteeum et al., Production of Single Cell Protein from Ethanol by Fed-Batch Process, Biotechnol. & Bioengineering, v. 21 (1979), pp. 1221–1237.

A. Einsele, et al., Substrate Uptake Mechanisms for Yeast Cells: A New Approach Utilizing a Fluorometer, European J. Appl. Microbiol. & Biotechnol., v. 6 (1979) pp. 335–339.

A. Einsele et a., Mixing Times & Glucose Uptake Measured with a Fluorometer, Biotechnol. & Bioengineering, v. 20 (1978), pp. 1487–1492.

D. W. Zabriskie, Use of Culture Fluorescence for Monitoring of Fermentation Systems, Biotechnol. & Bioengineering Symp. No. 9 (1979) pp. 117–123.

D. W. Zabriskie & A. E. Humphrey, Estimation of Fermentation Biomass Concentration by Measuring Culture Fluorescence, Applie & Environmental Microbiology, v. 35, No. 2 (Feb. 1978) pp. 337–343.

D. L. Ristroph, et al., Experience in the Use of Culture Fluorescence for Monitoring Fermentations, J. Ferment., Technol., v. 55, No. 6 (1977), pp. 599–608.

S. K. Maneshin and A. A. Arevshatyan, Change in the Fluorescence Intensity of NAD-H2 in Candida Guilliermondii in the Transition from an Anaerobic to an Aerobic State, Prikladnaya Biokhimiya i Mikrobiologiya, v. 8, No. 3 (May–Jun. 1972), pp. 323–326. (English translation).

D. E. F. Harrison and B. Chance, Fluorimetric Technique for Monitoring Changes in the Level of Reduced Nicotinamide Nucleotides in Continuous Cultures of Microorganisms, Applied Microbiol. (Mar. 1970), pp. 446–450.

D. W. Good and G. G. Vurek, Picomole Quantitation of Ammonia by Flow-Through Fluorometry, Analyt. Biochem., v. 130 (1983), pp. 199–202.

R. Sutherland, et al., Preliminary Results Obtained with a No-Label, Homogeneous, Optical Immunoassay for Human Immunoglobulin G Analytical Letters, v. 17 (BL) (1984), pp. 43–53.

Fluorosensor: The New Way to Look into Cells. Appliccation (Manual). Ingold Co.

F. P. Milanovich & T. Hirschfeld, Remote Fiber Fluorimetry: Using Optics for On-Stream Analysis, InTech, v 31, No. 3 (Mar. 1984), pp. 33–36.

B. K. Lok, et al., Total Internal Reflection Fluorescense: A Technique for Examining Interactions of Macromolecules with Solid Surfaces, J. Colloid and Interface Sci., v. 91, No. 1 (Jan. 1983), pp. 87–103.

B. K. Lok et al., Protein Adsorption on Crosslinked Polydimethylsiloxane Using Total Internal Reflection Fluorescense, J. Colloid & Interface Sci., v. 91, No. 1 (Jan. 1983), pp. 104–116.

R. M. Sutherland et al., Immunoassays at a Quartz-Liquid Interface: Theory, Instrumentation and Preliminary Application to the Fluorescent Immunassay of Human (List continued on next page.)

OTHER PUBLICATIONS

Immunoglobulin G, J. Immunol. Methods, v. 74 (1984), pp. 253-265.

B. Bosacchi and R. C. Oehrle, Resonant Frustrated-Total-Reflection Technique for the Characterization of Thin Films, Applied Optics, v. 21, No. 12 (15 Jun. 1982), pp. 2167-2173.

R. A. Van Wagenen, et al., Probing Protein Adsorption II. Total Internal Reflection Intrinsic Fluorescence, from ACS Advances in Chemistry Series, Morphology, Structure and Interactions of Biomaterials, S. L. Cooper, et al., eds. (1981).

P. L. Smock, et al., Vapor Phase Determination of Blood Ammonia by an Optical Waveguide Technique, Analytical Chemistry, v. 51, No. 4 (Apr. 1979), pp. 505-508.

Fluorofacts Data Sheets, BioChem Technology, Inc.

A. Rein and P. Wilks, Jr., Cylindrical Internal Reflection Cell, American Laboratory (Oct. 1982), pp. 152-155.

P. A. Wilks, Jr., Sampling Method Makes On-Stream IR Analysis Work, Industrial Research & Development (Sep. 1982), pp. 132-135.

Fiber Optics Simplify Remote Analysis, Chem. & Engrg. News (Sep. 27, 1982) pp. 28-30.

Remote Spectrometry with Fiber Optics, Science, v. 218 (26 Nov. 1982) pp. 875-876.

J. I. Peterson & G. G. Vurek, Fiber-Optic Sensors for Biomedical Applications, Science (13 Apr. 1984), pp. 123-127.

R. Chabay, Optical Waveguides, Analytical Chemistry, v. 54, No. 9 (Aug. 1982), pp. 1071A-1080A.

M. N. Kronick and W. A. Little, A New Immunoassay Based on Flourescence Excitation by Internal Reflection Spectroscopy, J. Immunological Methods, v. 8 (1975), pp. 235-240.

Attenuated Total Reflectance, In Treatise on Analytical Chemistry, Second Edition, P. J. Elving, ed. v. 7 pp. 313-323.

B. Chance, et al., Damper Sinusoidal Oscillations of Cytoplasmic Reduced Pyridine Nucleotide in Yeast Cells, Proc. Nat. Acad. Sci., v. 51 (1964), pp. 1244-1251.

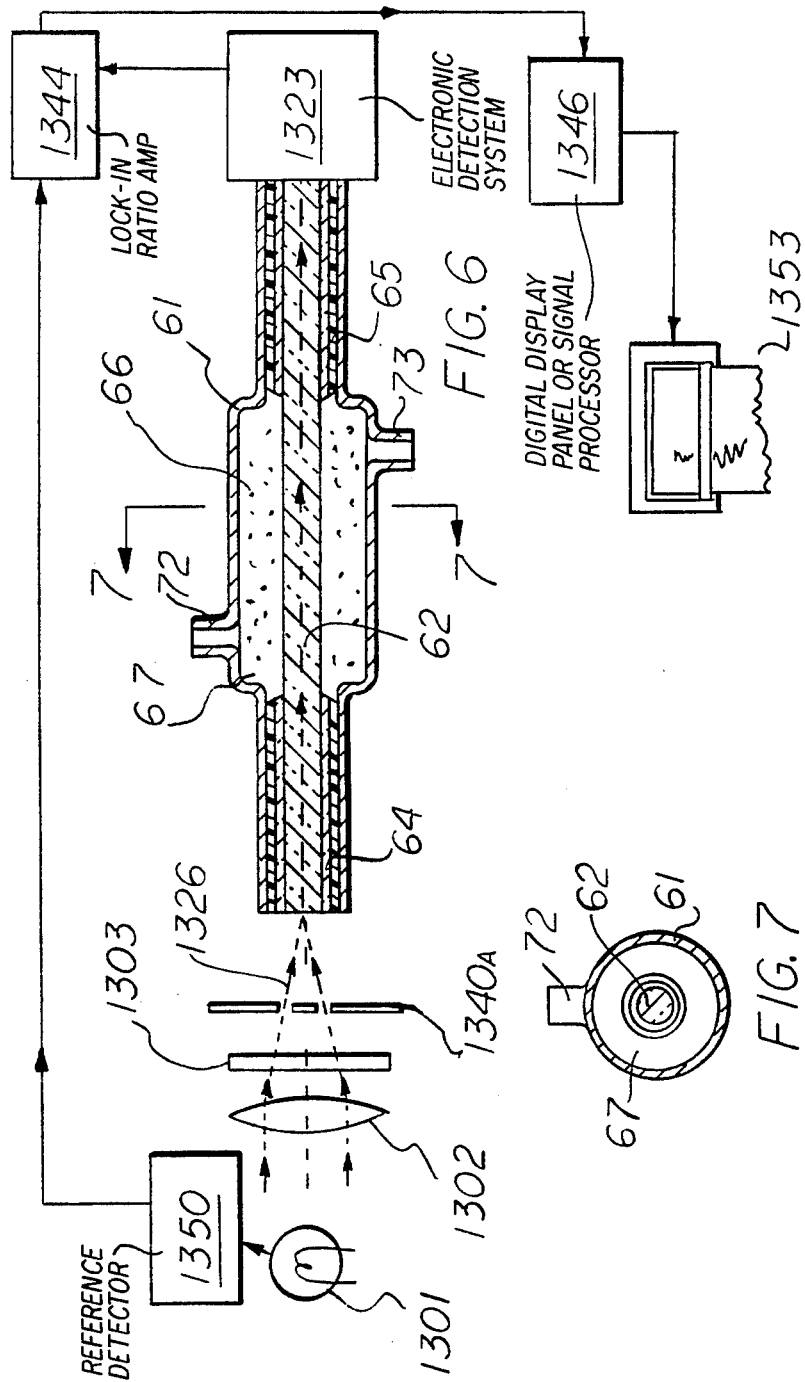

EVANESCENT WAVE BACKGROUND FLUORESCENCE/ABSORBANCE DETECTION

Continuation-in-part of Ser. No. 06/818,721, Jan. 14, 1986, now abandoned.

BACKGROUND OF THE INVENTION

1. Field of the Invention

The present invention relates to method and apparatus for the detection and measurement of certain optical characteristics of biological culture and fermentation media in a bioreactor or the like, and more particularly, to the measurement of the fluorescence and/or absorbance of a continuous phase in the presence of a discontinuous phase.

2. Description of Related Art

Fluorescence of intracellular NADH or NADPH has been shown to be a good indicator of the metabolic state of cells in culture, as well as serving as an indicator of the concentration of cells in the culture medium. Several papers have attested to the value of this kind of in situ measurement for both microbial and yeast culture applications. See, e.g., W. B. Armiger et al., Analysis and Control of Fed-Batch Fermentations Producing *Escherichia coli* Using Culture Fluorescence, Proceedings Biotech 84, Washington, D.C. 1984. Apparatus for performing these measurements is available from Bio-Chem Technology, Inc., Malvern, Pa., as the FluoroMeasure TM System.

From an economic point of view, it would be advantageous to use lower cost complex nutrients, such as molasses or corn steep liquor in industrially significant cultures. These, however, introduce additional background fluorescence. If the medium contains a fluorescent component which does not change during the course of the culture, a background correction can be made simply by subtracting the reading at time zero from all subsequent readings. In a case where the fluorescence of the media changes due to use by the cell or in the case where the cells produce a competing fluorescence, it becomes more difficult to correct on-line for changes in background. This can be done for a batch culture by taking serial samples, removing the cells and measuring the fluorescence of the medium. Even more difficult are background corrections in cases of continuous culture or where nutrients are added stepwise during the culture.

For fluorescent media, it would be useful to be able to determine how the fluorescence of the media is changing during the fermentation, such that a measurement can be made to the metabolic state of the cells and their growth rate. What is needed is a means of effecting the separation of the cell fluorescence from that of soluble materials.

Optical sensors for fermentations or tissue culture are capable of giving information on intracellular substances and conditions. Such information would permit a finer control based on actual intracellular information rather than on the existing on-line sensors, temperature, pH, dissolved oxygen, off-gas analysis. It would lead to a better scaleup and commercialization of products derived from recombinant DNA and cell fushion technologies. Optical sensors, at present, work best with media which do not interfere since there is not easy way to correct for changes in optical background.

The early work with optical sensors for following intracellular metabolism dates back to 1957, when Duysen and Amesz observed that the fluorescence of baker's yeast was similar to that of NADH and that the fluorescence of starved yeast could be enhanced by adding ethanol or glucose to the suspension. Later, Harrison and Chance built an instrument capable of measuring culture fluorescence in situ and could monitor aerobic/anaerobic transitions in continuous culture. Using a similar device, Humphrey and coworkers, and others, have shown that a fluorometer placed on a fermentor could measure intracellular NADH changes and might be useful for process control. Zabriskie and Humphrey showed the linear relationship between the logarithm of the fluorescence of the culture and the logarithm of cell concentration. Ristroph et al. studied the relationship between culture fluorescence and the growth of *Candida utilis* in a fed batch fermentation.

These studies have shown that the concentration in intracellular NADH measured by culture fluorescence in a fermentation is a function of the number of cells, the energy level within each cell, and the level of metabolic activity. A mathematical expression which is derived from these studies is:

$$F(t) = [Y_{f/x}(1 + m(t))]X(t) + E(t)$$

$X(t)$ is the cell concentration. The term in square brackets is the fluorescence yield, which is made up of an invariant compound $Y_{f/x}$, which is characteristic of the type of organism and a variable component $m(t)$, which changes in response to shifts in the level of metabolic activity. The final term, $E(t)$, with which the present invention is mainly concerned, is the environmental, or background, fluorescence. Obviously, if $E(t)$ fluctuates during the fermentation, then it would be difficult if not possible to derive information about the cells from the measured overall fluorescence. Continuous, or batch fed fermentation or cell cultures only exacerbate the problem. In those techniques, additional variables are introduced without corresponding information as to concentration.

Almost all of the published studies have used synthetic media where $E(t)$ is low, or the corrections for $E(t)$ had to be arrived at empirically, In scaling up fermentations and cell cultures for commercial production, economic factors may dictate use of the natural nutrients, like molasses or fetal calf serum, which have a natural fluorescence and therefore contribute to the background value. When checking some of the assumptions used in correcting for the background, I found indications that the background fluorescence of, for instance, molasses, and the fluoresence of yeast cells do not add linearly. This pointed up the need for a method for continuously measuring the media fluorescence background on-line and in real time, i.e. using a sensor or sensors continuously monitoring the detected variable as the fermentation or culture is being conducted.

This means that, without physically separating the cells from the media, a method was needed which caused the media to fluoresce without, at the same time, causing the cells to fluoresce. In accordance with the present invention, the evanescent wave phenomenon is used to meet this need.

SUMMARY OF THE INVENTION

When a beam of light is totally reflected from a non-mirrored interface between two optically transparent media of different refractive indexes, an evanescent wave phenomenon, such as shown in FIG. 1, exists. The light beam 11 is totally reflected from this kind of surface, unlike a mirrored surface, and behaves as though it penetrates for about half a wavelength into the less dense medium 12, e.g. an aqueous medium. Reference numeral 15 identifies the portion of light beam 11 that is the evanescent wave in the less dense medium 15. Reference numeral 16 identifies a measuring arrow showing a distance that is one wavelength of the light beam 11.

FIGS. 1 and 2 schematically show that the reflected beam is slightly displaced from where it would be if reflected from a mirrored suface. This displacement has been shown experimentally, and it is one of the proofs of the existence of the evanescent wave. This part of the light beam has many characteristics of a standing wave parallel to the surface. FIG. 3 shows how the intensity decreases with distance from the surface.

In FIG. 3, N is the incident wave, R is the reflected wave $\theta$ is the angle of incidence (which is greater than $\theta_c$, the critical angle. Z is the distance axis in the rarer medium measured from the interface with the more dense medium. $E_o$ is the initial magnitude of the electric field component of the light at zero depth in the rarer medium. dp is the depth of penetration, defined as the distance required for the electric field to fall to $e^{-1}$ of its value at the surface. The value of dp is directly related to the wave length in the denser medium and is inversely proportional to the angle of incidence and top the ratio of refractive indexes of the two media. The greatest strength of the evanescent wave occurs at the surface, and it decreases exponentially with distance from the surface.

It can be absorbed by an appropriate colored material, and if the material is fluorescent, it can excite the material to fluoresce. At the wave length of interest, 340 nm, the volume in liters swept out by this evanescent wave over a one square centimeter area would be $1.7 \times 10^{-8}$ liter. For a 200 $\mu$m diameter optical fiber 2.5 cm long, the swept volume would be $1.3 \times 10^{-11}$ liter.

The present invention accomplishes this separation by using the characteristics of the evanescent wave which forms in the less dense medium when light is totally reflected from the interface between two optically transparent substances of different refractive indexes. It makes use of my observation that it is unlikely that an intact cell will be in the volume of fluid swept by the evanescent wave next to the optical wavelengths since the wave penetrates approximately only $\frac{1}{3}$ to $\frac{1}{2}$ of a wavelength into the aqueous layer. The present invention therefore contemplate measurement of the fluorescence of the medium without interference from the intracellular fluorescence or from fluorescence of particles in solution.

The same concept is also adapted to measuring the optical absorbance of the medium independent of cells and particulate material. This can significantly reduce the complexity of the computer programs needed to deconvolute the data and thereby make the control of fermentation and tissue culture easier to achieve.

At the usual concentration of cells in a bioreactor, it is unlikely, as I said, that a cell would be in this small volume of fluid at any given time. Also, since, at an excitation wavelength of for example 280 nm, the evanescent wave only penetrates about 110 to 170 nm into the liquid phase, even if the cell is resting right on the surface of the optical wave guide, very little of the cell volume (mostly the cell wall or cell membrane), will interact with the evanescent wave. Thus, by limiting the volume that can interact with the light wave to that within the evanescent wave, the present invention provides, in effect, a separation of the intracellular fluorescence or absorbance from the fluorescence or absorbance of the media.

It is an object of this invention to facilitate the opening up of fermentation and cell culture to intracellular optical measurement under a wider variety of culture conditions because there will be a way to correct continuously for environmental or background changes on-line in real time.

It is a further object of the present invention to provide for the separation of the optical effects of intracellular contents from the optical effects of the culture medium.

It is a further object of the present invention to follow changes in the culture medium without interference from changes in the intracellular contents.

It is a further object of the present invention to follow changes in the intracellular contents without interference from changes in the culture medium.

It is a still further object of the present invention to reduce costs of monitoring the fluorescence of cell cultures.

It is a still further object of the present invention to simplify and shorten the time for scaleup or change of media in a fermentation, since separate, offline empirical measurements of background or environmental fluorescence will not have to be made. By a single test run, culture conditions might be brought to a preliminary optimization by appropriate additions of media components.

It is a still further object of the present invention to provide information about the extent of cell rupture, whether due to shear forces or other mechanical or chemical causes. In accordance with the present invention, the effect of stirring forces on cell integrity could be measured on-line in real time, allowing corrections to be made during a fermentation run rather than after the run when data shall been subsequently analyzed.

It is a still further object of the present invention to permit the use of optical absorbance methods for following other non-fluorescent intracellular materials, since the ability to correct for background would provide the equivalent of a continuous dual beam spectrophotometer.

It is a still further object of the present invention to provide for the better control of the concentration of individual nutrients in the culture media through the improved ability to follow specific changes of optically differentiable materials in the medium.

It is a still further object of the present invention to significantly improve the yield of fermentation and tissue cultures, reduce the time and cost of scaleup, allow for a more precise control based on the state of the intracellular metabolism, and speed up the commercialization of new recombinant DNA and cell fushion technologies through more efficient fermentation and tissue culture techniques.

BRIEF DESCRIPTION OF THE DRAWINGS

FIG. 6 is a partially schematic illustration of another embodiment of the present invention.

FIG. 7 shows the portion of the embodiment of FIG. 6 viewed from a right angle to the view of FIG. 6, taken along line 7—7.

DETAILED DESCRIPTION

Figure 1:
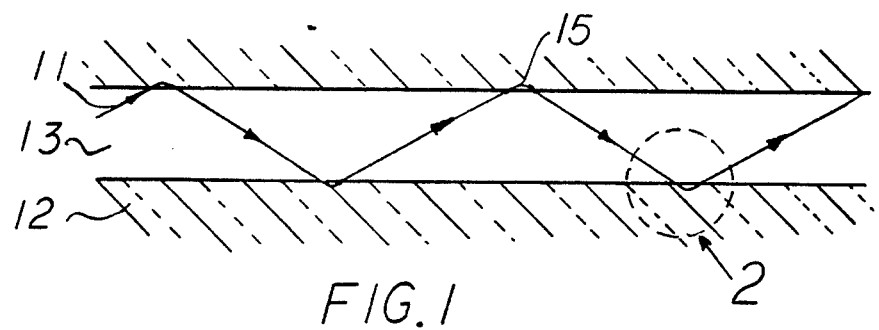
FIG. 1 is a schematic illustration of the evanescent wave phenomenon, wherein a light beam 11 traverses a path from left to right through a wave guide 13 such as an optical fiber.
Figure 2:
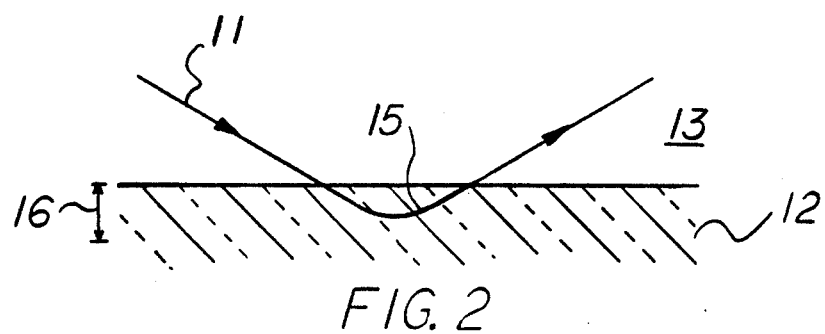
FIG. 2 is an enlarged view of the circular area 2 within FIG. 1.
Figure 3:
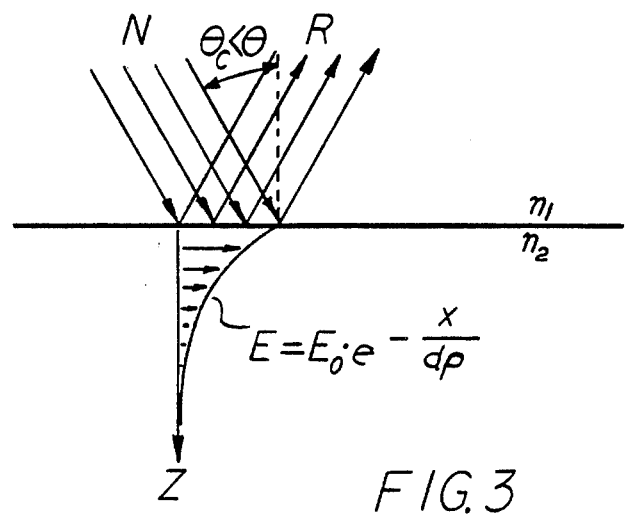
FIG. 3 is a schematic illustration of the variation of intensity of the evanescent wave with distance from the interface between the two media.
Figures 4, 5:
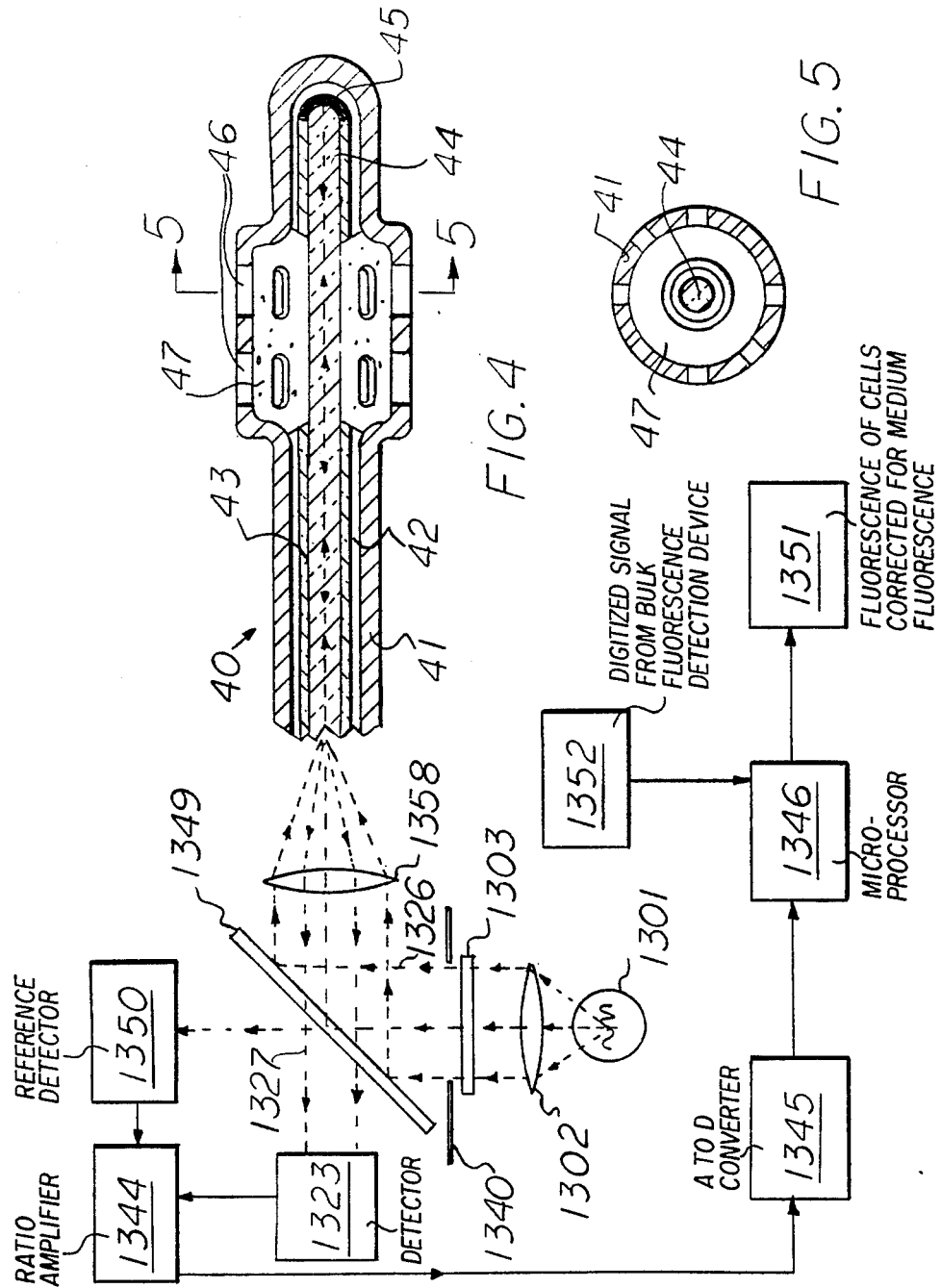
FIG. 4 is a partially schematic illustration of a cross-sectional elevation of one of the variations of the present invention employing a metal sheathed optical fiber that may be dipped into a liquid medium.
FIG. 5 is a cross sectional side elevation of the embodiment shown in FIG. 4 viewed from a right angle to the view of FIG. 4, taken along the cross sectional line 5—5.

The embodiment of the invention shown in FIGS. 4 and 5 provides a relatively simple means of determining the background fluorescence of a solution containing particulate matter by dipping into the liquid a dipstick 40 which comprises a metal housing 41 surrounding an optic fiber 44 through which an evanescent wave of light is used to excite the fluorescence of the solution. The housing 41 defines a chamber 47, into which the solution to be tested passes through apertures 46 in the housing 41.

On the portion of the optic fiber 44 within the chamber 47, the opaque sheath 42 and transparent cladding 43 have been removed, exposing the fiber 44 directly to the solution within the chamber 47.

To illuminate the fiber 44, there is provided a light source 1301 of either visible or invisible light, such as an incandescent lamp or laser, an excitation beam lens 1302, and an excitation beam filter 1303, arranged as shown in FIG. 4.

The radiation from the light source 1301 passes through the lens 1302, where it is collimated, and then passes through the filter 1303, where it is filtered into a monochromatic excitation beam 1326 of desired wavelength (schematically illustrated by dashed lines with arrows) and passes through an aperture in plate 1340.

The excitation beam 1326 thereupon encounters a dichroic mirror 1349 adapted to reflect the wavelength of light represented by the excitation beam 1326 into the excitation-emission beam lens 1358, where the beam 1326 is decollimated and directed into proximal end of optic fiber 44, which may extend from the metal housing 41 if desired. As stated above, the excitation beam 1326 travels through optic fiber 44 until it reaches the distal end, where it encounters a light trap 45, e.g. of black silicone rubber.

The evanescent wave portion of the excitation beam 1326 traveling down the optic fiber 44 encounters the molecules of solute within chamber 47 that are immediately adjacent the fiber 44 (i.e. within about $\frac{1}{8}$ to $\frac{1}{2}$ wavelength as discussed above) and, to the extent that it is susceptible, excites the solute to emit fluorescence.

Such fluorescence passes into the optic fiber 44 and travels to its proximal end as the emission beam 1327, where it exits the optic fiber 44, encounters the excitation-emission beam lens 1358 and is collimated. The beam 1372 then passes through the dichroic mirror 1349, which has been fashioned to pass the wavelength of the light emitted by the fluorescence of the solute to be measured.

The emission beam then impinges upon an electronic detection system 1323 such as a photomultiplier tube in counting mode. The detection system 1323 is selectively responsive to the wavelength of the emission radiation because a filter or monochromator is incorporated therein. The electronic detection system 1323 generates a signal that is sent to a lock-in ratio amplifier 1344. A reference detector 1350, which detects the intensity of the excitation beam 1326, also generates a signal that is sent to the lock-in ratio amplifier 1344, where the two signals are processed conventionally to compensate for variations in the intensity of the excitation beam 1326.

The signal from the lock-in ratio amplifier 1344 is transmitted to an analog-to-digital converter 1345, which generates a signal fed to a digital display panel or signal processor 1346. Desirably an additional digital signal 1352 from a conventional device reading bulk fluorescence (of the solution and any particulate matter in it) is generated and similarly fed to the display panel or processor 1346. The signal 1352 may, for example, be from a Fluoromeasure ™ fluorometer (BioChem Technologies, Inc., Malvern, Pa.). When the data in signal 1345 is subtracted from the data in signal 1352, the resulting data sent to element 1351 describes the fluorescence of the particulate matter, inasmuch as fluctuations in the fluorescence of the solute have been subtracted from the fluorescence of the bulk.

An alternative embodiment shown in FIGS. 6 and 7 utilizes an optic fiber 62 within a housing 61 defining a chamber 67 having a pair of ports 72, 73. The slurry to be subjected to optical measurement in accordance with the present invention may be introduced through inlet port 72 and exhausted through outlet port 73. Desirably the chamber 67 is designed so that flow therethrough is essentially laminar.

As in the embodiment previously described (FIGS. 4 and 5), light from a light source 1301 passing through a lens 1302 and filter 1303 is introduced into the end of the fiber optic 62. However, to maximize the evanescent wave relative to the radiation traveling straight through the fiber optic 62, a plate 1340A, having an O-shaped aperture, with a filled-in center, may be used rather than one having a circular cutout. This will block rays from entering the fiber optic 62 along the axis.

In this configuration, a reference detector 1350 is disposed along a different path from the light source 1301 than that traveled by the excitation beam 1326 so that variations in the intensity of the light source can be detected and fed to a lock-in ratio amplifier 1344 as is conventional.

At the distal end of the fiber optic 62, an electronic detection system 1323 is placed to receive light therethrough. The detection system 1323 may be set up to detect the intensity of light of the wavelength of the emission beam 1326. In that event, it will generate a signal useful in determining the absorbance of the solute in solution, free of cellular or other particulate matter. The absorbance information may be related to the concentration of a solute that is to be monitored, or it may be a background figure which may appropriately be subtracted from another absorbance reading to provide useful data.

Alternatively the detection system 1323 may be set up with an appropriate filter or monochromator to detect a wavelength of radiation which is emitted by a solute as fluorescence, in which event the resulting data will be similar to that generated by the embodiment of the invention shown in FIGS. 4 and 5.

Similarly to the previously described embodiment, the signal from detection system 1323 is supplied to the lock-in ratio amplifier 1344, and the output thereof is directed to a display panel or processor 1346, the output of which may, for example, be fed to a chart recorder 1353 as shown.

Using the evanescent wave phenomenon, the embodiment of the present invention shown in FIGS. 8 to 11 is capable of determining both absorbance and fluorescence in such quick alternating succession as to provide virtually simultaneous readings. With a flat plate 1316 as the wave guide, the device housed in detector enclosure 1332 is particularly adapted to be used in a reactor or fermentation vessel 1312 for realtime determination of several variables which assist in determining the instantaneous concentration of various components of the contents of the vessel 1312.

The detector enclosure 1332 is mounted within a conventional pipelike mounting port 1362 extending from the reactor vessel wall 1312. The distal end of mounting port 1362 is threaded to mate with grommet 1333, which secures the enclosure 1332 to the port 1362 and thereby to the reactor vessel wall 1312.

Depending on the length of the mounting port 1362 and the depth to which it is desired that the detector housing 1332 penetrate beyond the vessel wall 1312 into the reaction mixture 1314, a rubber-like O-ring 1311 is interposed within any of three O-ring grooves 1361 to seal the retainer sleeve 1354 of housing 1332 watertight within the port 1362.

A screw-threaded wave guide plate mounting sleeve 1336 mates with the retainer sleeve 1354 and holds the wave guide plate 1316 securely in place. An insert 1335, which may be one of optionally several lengths, extends the wave guide plate mounting sleeve 1336 so that the wave guide plate 1316 extends the desired distance into the reaction mixture 1314 beyond vessel wall 1312.

A fluorescence enclosure 1308 extends outwardly from the vessel wall 1312, screw-threaded to the insert 1335. Enclosed within the aforesaid elements are optical fiber elements 1305, 1317, 1319 and 1320, which convey light to and from the wave guide plate 1316. The optical fiber elements 1305, 1317, 1319 and 1320 pass through fluorescence enclosure cover 1307, which is held in place by a fluorescence enclosure cover retainer bezel 1309.

The light source 1301, lens 1302, filter 1303 and aperture 1340 are generally as have been described above.

Figure 8:
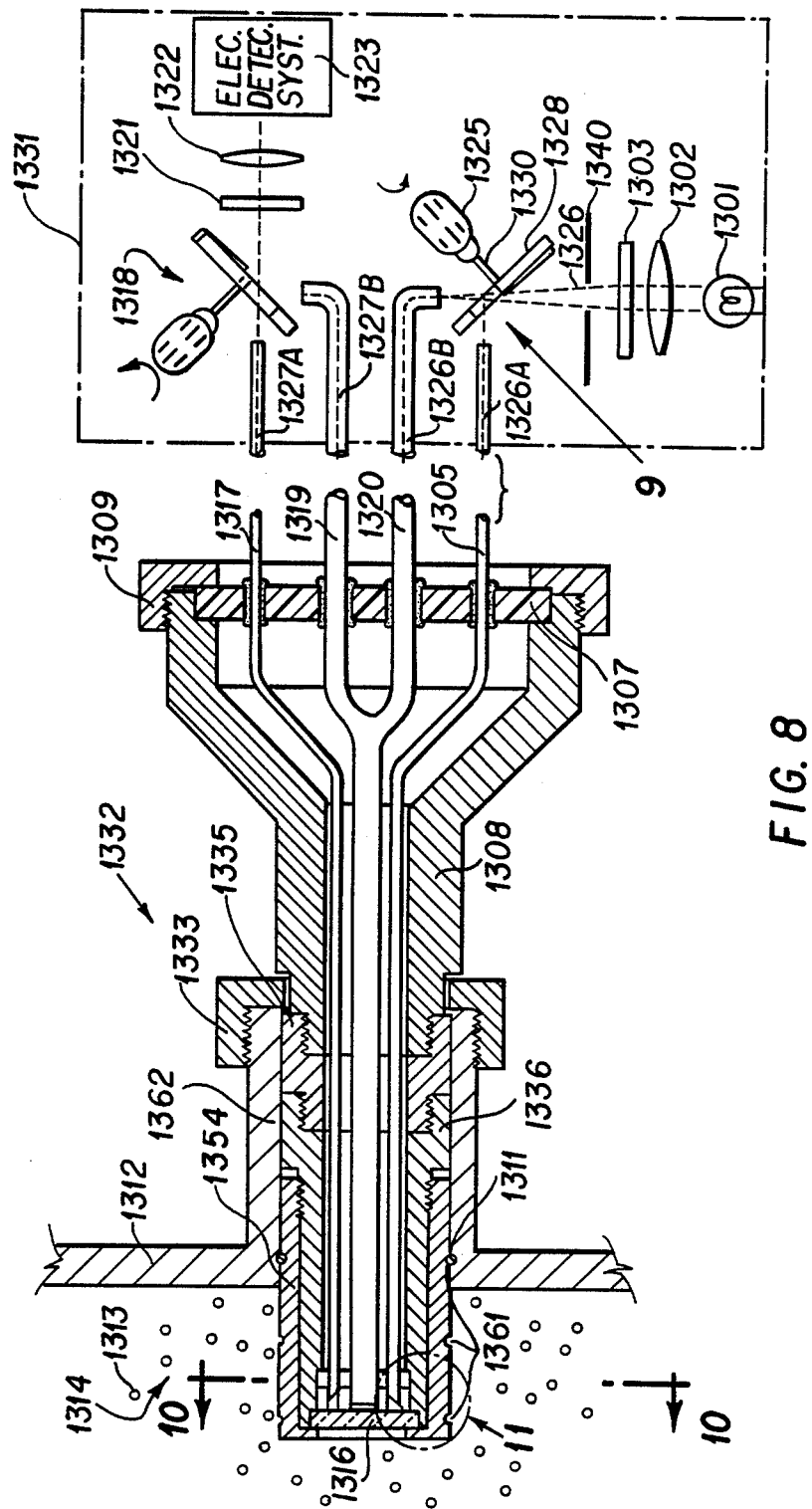
FIG. 8 is a partially schematic illustration of a cross-sectional elevation of a preferred embodiment of the present invention wherein the optical waveguide is a flat plate 1316, and a barrier 1312 confines the liquid to one side of the waveguide.
Figure 9:
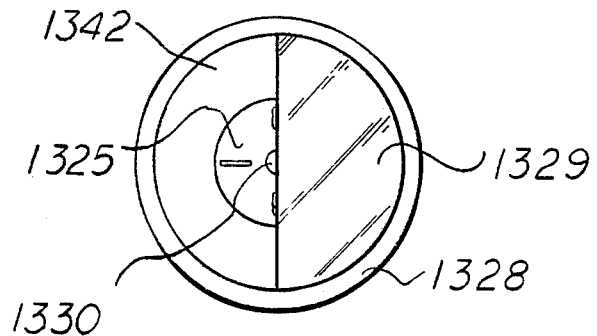
FIG. 9 is an elevation view of the disk 1328 shown in FIG. 8 taken along the line 9.
Figure 12:
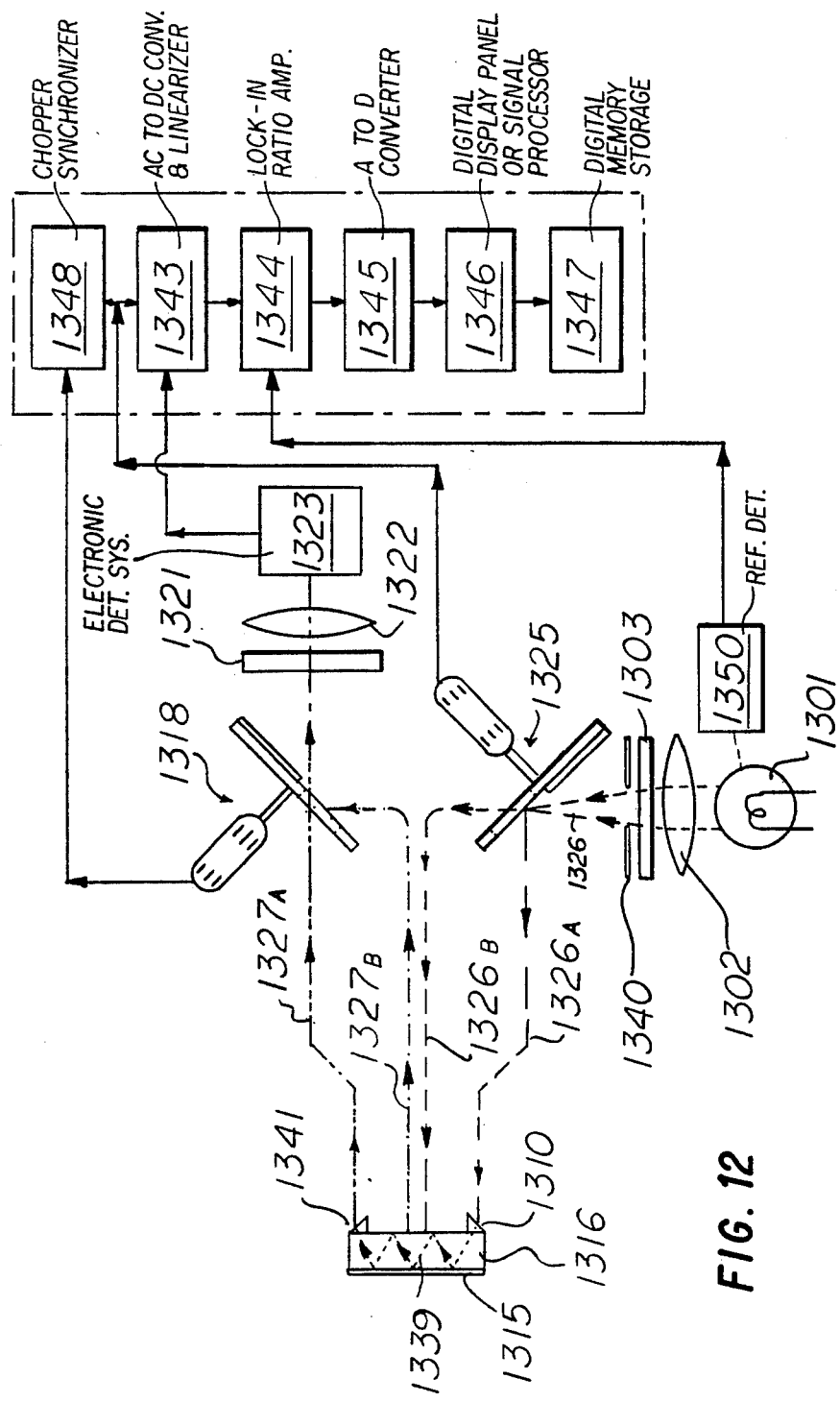
FIG. 12 is a schematic illustration of the embodiment of FIG. 8 showing the paths of light rays and the steps of processing of data.

As shown schematically in FIG. 12 as well as generally in FIG. 8, an excitation beam light chopper 1325 is interposed in the optical path to pass the focused excitation beam 1326 to the evanescent wave excitation fiber optic 1305 and then to the direct wave excitation fiber optic 1320 in alternating succession. As shown more particularly in FIG. 9 the excitation beam light chopper 1325 comprises a disk 1328 having mounted thereon a semicircular mirror 1329, the other half of the disk 1328 having an opening 1342 sufficiently wide to allow the excitation beam 1326 to pass through to the optical fiber 1320.

The chopper disk 1328 is rotated by a shaft 1330. As the disk 1328 rotates, the excitation beam 1326 is directed into two alternate paths. When the excitation beam 1326 is incident on the mirror 1329, the beam follows path 1326A directed to optic fiber 1305. Alternately, when the disk 1328 has rotated to a position where the excitation beam 1326 is incident on the opening 1342, it passes through to the optical fiber 1320.

The optical fiber 1305 carries the excitation beam 1326A from the sealed, light-tight housing 1331, to fluorescence detector enclosure 1332. The optical fiber 1305 typically consists of several individual fibers completely surrounded by a flexible transparent cladding 1306 and an opaque flexible sheath 1304. The refractive index of the transparent cladding 1306 is slightly less than that of the optic fiber 1305.

Figure 10:
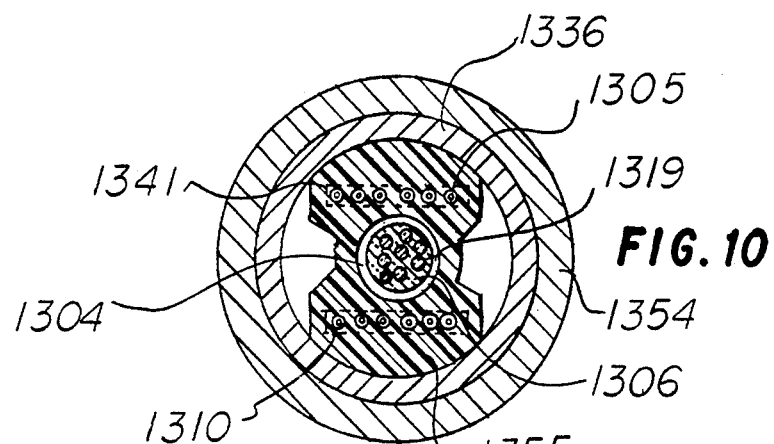
FIG. 10 is a cross sectional side elevation of the embodiment shown in FIG. 8 viewed from a right angle to the view of FIG. 8, taken along the cross sectional line 10—10.
Figure 11:
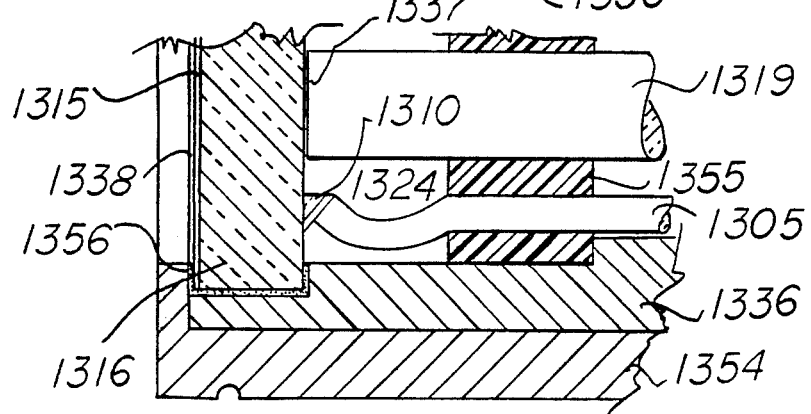
FIG. 11 is an enlarged view of the area 11 within FIG. 8.

After passing through grommet 1333, the individual optical fibers of the optic fiber 1305 pass through a mounting block 1355 where they are spread out, as shown in FIG. 10. Optic fiber mounting block 1355 is desirably injection molded of a plastic capable of withstanding sterilization temperature of about 140° C., e.g. polysulfone.

The individual fibers of optical fiber 1305 that are in contact with the prism 1310 along its oblique surface are cut square to the longitudinal axis of the fibers. The mounting block 1355 holds the fiber bundle 1305 such that the light enters at right angles to the oblique surface of the prism 1310. The angle of the oblique surface of prism 1310 to the side of the prism in contact with the flat plate wave guide 1316 is such as to introduce the light beam 1326A into the flat plate wave guide 1316 at an angle greater than the critical angle, so that the light beam 1326A will be confined to the flat plate wave guide and will generate an evanescent wave at the interface of the wave guide 1316 and the reaction medium 1314 in contact with the wave guide.

Prims 1310 is rectangular and has the same refractive index as the flat plate wave guide 1316. The loss of intensity of excitation beam 1326 during its transition from the optic fiber 1305 to the prism 1310 is minimized by having the sides of the prism 1310 greater than the diameter of the optical fiber 1305 and by having the transitional interface between the optic fiber 1305 and the slanted surface of the prims 1310 covered by a liquid 1324 having same refractive index as that of the prism 1310.

The flat transparent side of the prism 1310 is cemented to the distal face 1337 of the flat plate wave guide 1316 by utilizing a transparent cement having a same refractive index as that of prism 1310 and flat plate wave guide 1316. The actual angle of the oblique surface of prims 1310 is a function of the refractive indices of the materials used for prism 1310 and the flat plate wave guide 1316. The flat plate wave guide 1316 is circular in cross section and is typically made of bubblefree and distortion-free material such as quartz. The two parallel faces 1337 and 1338 are optically polished to a high degree and are truly parallel within the normal manufacturing tolerances. The cylindrical side wall of the flat plate wave guide 1316 is significantly less in height than its diameter.

The flat plate wave guide 1316 is sealed along its side wall by an opaque seal 1356 of PTFE polymer (e.g. Teflon or the like) to prevent loss of light and also act as a sealent. The frontal side 1338 of the flat plate wave guide 1316 is coated with a very thin and hard transparent layer 1315 of material such as Surlyn (Dupont), deposited diamond etc. The thickness of the wave guide coating 1315 should be such as to have no effect on the penetration of the evanescent wave 1339 into the medium 1314. The wave guide coating 1315 is desirable to prevent the adherence of cellular products generated by the particulate matter 1313 or the dirt present in the medium 1314. The wave guide coating 1315 also prevents damage such as scratches to the frontal side 1338 of the flat plate wave guide 1316.

An evanescent wave 1339 is created within the flat plate wave guide 1316 when the excitation beam 1326 is repeatedly reflected between the two non-mirrored surfaces 1337 and 1338 respectively. The evanescent wave 1339 so generated penetrates into the medium 1314 under observation through the frontal side 1338 of the flat plate wave guide 1316. As explained above, the evanescent wave only penetrates a distance up to about half of a wave length of the excitation beam 1326 into the medium 1314 under observation. The discrete particulate matter 1313 such as cells present in the medium 1314 has virtually no interaction with the evanescent wave 1339.

There is a prism arrangement 1342 similar to prism 1310 at the opposite end of the flat plate wave guide 1316 along its distal side 1337 as shown in FIGS. 8 and 12. The thickness of the flat plate wave guide and the distance between the prisms 1310, 1341 is such that the incident light beam 1326A is refracted an integral number of times and exits through prism 1341. The ends of the individual fibers of fiber optic 1317 have been cut square to the longitudinal axis of the fibers. The mounting block 1355 holds the fiber bundle 1317 such that its longitudinal axis is at right angles to the oblique surface of prism 1341.

As an alternate construction, the flat plate wave guide 1316 and prims 1310, 1341 may be fabricated as a single unit. Moreover, alternatively to the relationship illustrated herein, wherein the faces of the prims 1310, 1341 are raised above the surface of the wave guide 1316, the oblique faces of the prisms may be recessed into the surface of the wave guide. As an additional alternative, two diametrically opposite edges of the wave guide plate may be beveled to serve an equivalent function to the oblique edges of prisms 1310 and 1341.

Individual fibers of the optical fiber 1317 are attached to an oblique surface of the prism 1341, the transitional interface consisting of a liquid film 1324 having a refractive index close to that of the flat plate wave guide 1316. The optical fiber 1317 then passes through the optic fiber mounting block 1355 and its cross section then becoming circular. The optical fiber 1317 then passes through the grommet 1333 and enters the source and detection housing 1331. In direct path of optical fiber 1317 as shown in FIG. 8 there exists a light chopper assembly 1318 which is constructed similarly to excitation light chopper 1325. Next to the light chopper assembly 1318 in the same direction there is an emission beam filter 1312 which eliminates all the nonfluorescent light, followed by the emission beam lens 1322 which focusses the emission beam 1327 on an electronic detection system 1323.

FIG. 12 is a schematic representation of the light path in the embodiment of the present invention shown in FIG. 8. The light beam 1326 from light source 1301 is focused by a lens 1302 such that the light is properly coupled to the optical fibers bundles 1305 and 1320. In coupling light to the optical fibers or wave guides, attention must be paid to the numerical aperture ("NA") of the fiber optic or wave guide. It is a matter of matching the lens 1302 to the NA and the diameter of the fiber or fiber bundle or quartz wave guide.

Care must be taken to prevent the fiber cladding from acting as a wave guide. This can be achieved by sheathing the cladding with an opaque sheath. To get uniform distribution of light, the lens must confine the light uniformly across the input face of the fiber or wave guide. The light then passes through a slit or diaphragm and thence to chopper 1325.

Chopper 1325 then, by alternately interposing and removing the mirror 1329 from the excitation light beam 1326, divides the light beam 1326 into two paths, 1326A and 1326B.

Beam 1326A travels through fiber bundle 1305 to prism 1310, which couples the light beam properly to flat plate wave guide 1316 such that the light beam is guided by multiple internal reflection through the wave guide. The evanescent wave is absorbed by the solution components able to interact with light of the selected wavelength. The evanescent wave does not optically interact with or excite to fluorescence the particles 1313 suspended in the reaction medium 1314. Those solution components able to fluoresce will emit their fluorescence at or near the surface of the flat plate wave guide 1316.

A portion of the emitted light will couple into the wave guide and be transmitted through light path 1327A to chopper 1318. Light beam 1326B is transmitted via fiber bundle 1320 to the internal surface 1337 of the flat plate wave guide, which acts as a window; since the light impinges at right angle to the surface, it goes right through and illuminates the bulk suspension near the flat plate 1316, thus exciting to fluorescence both the solution 1314 and the particles or cells 1313 suspended therein which are able to fluoresce.

A portion of the emitted fluorescence beam 1327B passes back through the flat plate 1316 and enters fiber bundle 1319 and is guided to chopper 1318. Chopper 1318 is synchronized with chopper 1325 through synchronizer 1348 such that when chopper 1325 is diverting the light beam over pathway 1326A, chopper 1318 is configured to allow light through pathway 1327A to go through filter 1321 and lens 1322 to detector 1323. When chopper 1325 is diverting the light beam over pathway 1326B, chopper 1318 is configured to allow light through pathway 1327B to go through filter 1321 and lens 1322 to detector 1323.

Synchronizer 1348 also serves to synchronize the signal processing train with the chopper positions such that the signal processor is is treating the signal as is appropriate to the mode of generation of the signal, e.g. determination of evanescent wave fluorescence vis-a-vis determination of bulk fluorescence.

The signal from the detector 1323 and from synchronizer 1348 is fed, for example, to an AC to DC converter and linearizer 1343, then to a lock-in ratio amplifier 1344, where the amplitude of the signal is corrected for variations in the amplitude of the excitation beam detected by reference detector 1350, then to an analog-to-digital converter 1345, then to a digital display or signal processor 1345 and then to a digital storage or memory 1347.

If filter 1321 is constructed to pass the emitted fluorescence wavelength, then the device of the present invention measures fluorescence. If filter 1321 is constructed to pass the same wavelength as the excitation beam 1326, then the device measures the optical absorbance of the solution 1314.

In the event that it is desired that only fluorescence and not optical absorbance be measured, an alternative embodiment 1318 (not shown) may omit the chopper 1318 of FIGS. 8 and 12. In that event, light bean 1327A is merely trapped rather than being guided to filter 1321 and detector 1323. Fiber optic 1317, in such an embodiment, may be omitted and replaced with a light trap, or fiber optic 1317 may itself channel the light away from the flat plate wave guide 1316 as a light trap. Both the bulk fluorescence excited by light beam 1326B and the solution fluorescence excited by light beam 1326A generating an evanescent wave at the surface of the flat plate wave gude 1316 are transmitted over light path 1327B to filter 1321. Filter 1321 is selected to allow only the emitted fluorescent wavelength to pass through.

Figure 14:
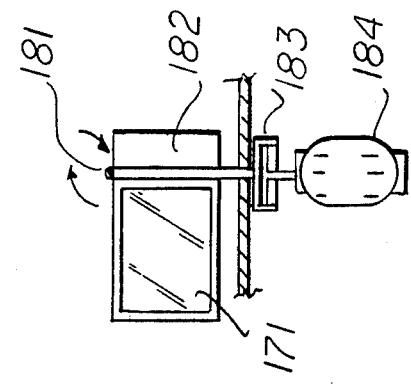
FIG. 14 shows a portion of the embodiment of FIG. 13 viewed from a right angle to the view of FIG. 13 taken along the line 14.
Figure 13:
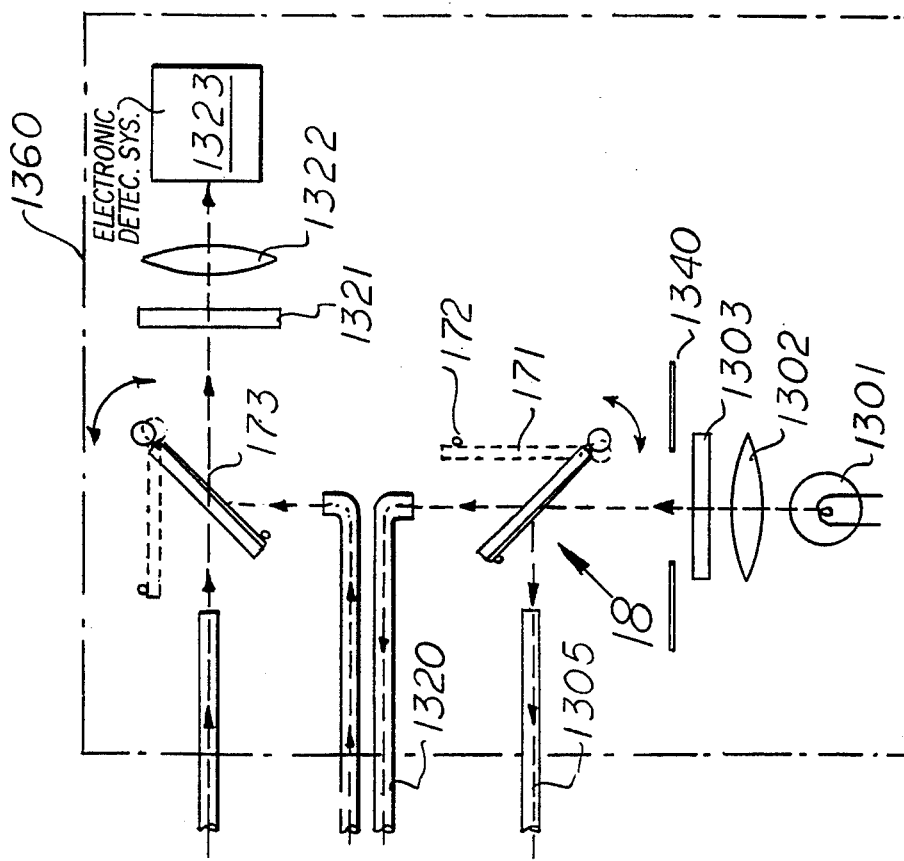
FIG. 13 is a schematic illustration of the contents of the source and detector housing of an embodiment alternative to the design shown housed in element 1331 of FIG. 8.

FIG. 13 illustrates yet another embodiment where the contents of housing 1360 are substituted for the contents of housing 1331 of the embodiment of FIG. 8. This embodiment is suitable for slow speed chopping of the light beams, for example, a few hertz or even fractions of a hertz. The chopping device viewed in the direction of arrow 14 is shown in FIG. 14. A flat plate 182 is affixed to a shaft 181, which is attached to a speed reducer clutch 183. The clutch 183 is attached to the shaft of reversible motor 184. A flat mirror 171 is attached to plate 182.

The plate 182 with mirror 171 attached is pivoted to swing between the position shown in FIG. 13 with solid lines or alternately the position shown with dashed lines. A stop 172 limits the travel of mirror 171 as the plate 182 abuts it and acts as a rigid point fixing the position of the mirror precisely again and again. Mirror 173 is similarly mounted for reciprocation and synchronized with mirror 171, generally as described with respect to the embodiment of FIGS. 8 and 12.

Having thus described my invention, what it is desired to protect by Letters Patent and hereby claim is:

1. A method for the optical analysis of a slurry, which slurry comprises:
   (a) a continuous phase which comprises a component that fluoresces at an optically detectable wavelength, and
   (b) a discontinuous phase which comprises a component that also fluoresces at said optically detectable wavelength,
   the method comprising the steps of:
   (i) optically exciting said slurry with an evanescent wave having a wavelength that excites the fluorescence of said components and simultaneously
   (ii) detecting the intensity of the fluorescence resulting therefrom, and then
   (iii) relating said detected intensity of fluorescence to the concentration of said component in said continuous phase, such that said detected intensity of fluorescence is independent of the concentration of the component in said discontinuous phase that also fluoresces.

2. A method for the optical analysis of a slurry, which slurry comprises:
   (a) a continuous phase which comprises a component that fluoresces at an optically detectable wavelength, and
   (b) a discontinuous phase which comprises a component that also fluoresces at said optically detectable wavelength,
   the method comprising the steps of:
   (i) optically exciting said slurry with an evanescent wave having a wavelength that excites the fluorescence of said components and simultaneously
   (ii) detecting the intensity of the fluorescence resulting therefrom, and at a different but nearby time
   (iii) illuminating the slurry with a non-evanescent wave and simultaneously
   (iv) detecting the intensity of the fluorescence or absorbance resulting therefrom, and then
   (v) determining the difference between the two intensity values, and
   (vi) relating said difference to the concentration of said component in said discontinuous phase, such that said difference is independent of the concentration of the component in said continuous phase that also fluoresces.

3. The method of claim 2 wherein the continuous phase comprises an aqueous solution in a bioreactor and the discontinuous phase comprises living cells.

4. The method of claim 3 wherein the fluorescence of NADH and NADPH are measured.

5. The method of claim 4 wherein the excitation beam is about 366 nm and the fluorescence is measured at about 460 nm.

6. Apparatus for determining the fluorescence or absorbance of the discontinuous phase of a system having a continuous phase which also fluoresces or absorbs light when excited or illuminated by light at an optically detectable wavelength emitted by the apparatus, comprising:
   (a) means for exciting the continuous phase with an evanescent wave at said wavelength, and
   (b) means for measuring the intensity of the fluorescence or absorbance resulting from the excitation of the continuous phase, and
   (c) means for illuminating the system with a nonevanescent wave at said wavelength, and
   (d) means for measuring the intensity of the fluorescence or absorbance resulting from the illumination of the system, and
   (e) means for comparing an intensity measurement generated by one of the aforesaid measurement means with an intensity measurement generated by the other of the aforesaid measurement means and for generating an indication of the difference between them,
   such that the value of said difference is related to the concentration of said component in said discontinuous phase, and such that said value is independent of the concentration of the component in said continuous phase that also fluoresces.

7. Apparatus of claim 6, further comprising:
   (f) means for deactivating said evanescent wave excitation means (a) before activating the measurement means (d) and for deactivating said illumination means (c) before activating the measurement means (b), such that measurement means (d) is active only during the illumination of the system by illumination means (c), and measurement means (b) is active only during the excitation of the continuous phase with evanescent wave excitation means (a).

8. Apparatus of claim 7, further comprising:
(g) a source of light at said wavelength,
(h) means for directing light from said source alternately to said excitation means (a) and to said illumination means (c),
(i) means for generating a signal having a value which is related to the intensity of light at said wavelength that is detected,
(j) means for directing light from the system to said signal-generating means (i), and
(k) means for detecting when the light-directing means (h) is directing light to said excitation means (a) and when it is directing light to said illumination means (c) and for alternately directing the signal from said signal-generating means (i) to said measuring means (b) whenever the light is directed to excitation means (a) and to said measuring means (d) whenever the light is directed to illuminating means (c).

9. Apparatus of claim 8, wherein the excitation means (a) comprises an optical fiber at least a portion of which is not covered with cladding.

10. Apparatus of claim 8, wherein the excitation means (a) comprises an optical plate.

11. Apparatus for determining the fluorescence or absorbance of the discontinuous phase of a system having a continuous phase which also fluoresces or absorbs light when excited or illuminated by light at an optically detectable wavelength emitted by the apparatus, comprising:

(a) a source of light at said wavelength, and a plate waveguide having a face in contact with said system,
(b) means for directing light from said source to said plate waveguide at an angle sufficiently oblique to said face to create an evanescent wave in said system, such that a first state of excitation of the system is created,
(c) means for directing light from said source to said plate waveguide at an angle approximately perpendicular to said face, such that a second state of excitation of the system is created,
(d) chopper means for alternately directing light from said source to said directing means (b) or said directing means (c),
(e) means for detecting light at a wavelength emitted by the system upon fluorescence,
(f) means for directing light from said plate waveguide at an angle approximately perpendicular to said face to said detection means (e),
(g) means for directing light from said plate waveguide at an angle oblique to said face to said detection means (e),
(h) chopper means for alternately directing light from said directing means (f) or said directing means (g) to said detection means (e),
(i) means for synchronizing chopper means (d) with chopper means (h), and
(j) means for processing the signal from detection means (e) to compare the value obtained during the first state of excitation with that obtained during the second state of excitation and to produce output related to the difference in said values.

12. Apparatus of claim 11 wherein said means for directing light (b), (c), (f) and (g) are fiber optics.

13. Apparatus of claim 12, wherein said means for directing light (c) and (f) together comprise a single bundle of optical fibers.

* * * * *